United States Patent
Woods et al.

(10) Patent No.: US 8,634,622 B2
(45) Date of Patent: Jan. 21, 2014

(54) COMPUTER-AIDED DETECTION OF REGIONS OF INTEREST IN TOMOGRAPHIC BREAST IMAGERY

(75) Inventors: Kevin Woods, Beavercreek, OH (US); Michael J. Collins, Beavercreek, OH (US); Senthil Periaswamy, Beavercreek, OH (US); Robert L. Van Uitert, Hollis, NH (US)

(73) Assignee: iCad, Inc., Nashua, NH (US)

( * ) Notice: Subject to any disclaimer, the term of this patent is extended or adjusted under 35 U.S.C. 154(b) by 1042 days.

(21) Appl. No.: 12/579,898

(22) Filed: Oct. 15, 2009

(65) Prior Publication Data
US 2010/0128950 A1    May 27, 2010

Related U.S. Application Data

(60) Provisional application No. 61/105,895, filed on Oct. 16, 2008.

(51) Int. Cl.
*A61B 6/03* (2006.01)

(52) U.S. Cl.
CPC ........................................ *A61B 6/03* (2013.01)
USPC ........................................................ 382/131

(58) Field of Classification Search
USPC ...................................... 378/20–25; 382/131
See application file for complete search history.

(56) References Cited

U.S. PATENT DOCUMENTS

| | | | |
|---|---|---|---|
| 2001/0038681 A1* | 11/2001 | Stanton et al. | 378/55 |
| 2003/0007598 A1* | 1/2003 | Wang et al. | 378/37 |
| 2005/0113681 A1* | 5/2005 | DeFreitas et al. | 600/426 |
| 2006/0153434 A1* | 7/2006 | Wang | 382/128 |
| 2009/0034684 A1* | 2/2009 | Bernard et al. | 378/98 |

OTHER PUBLICATIONS

Godfrey, Optimization and Clinical Implementation of Matrix Inversion Tomosynthesis (MITS) for the Detection of Subtle Pulmonary Nodules, 2005, Doctoral Dissertation, Duke University, Department of Biomedical Engineering, 164+ pages.*
Talwar, Incremental Overlapped Reconstruction, 1993, 1993 IEEE Conference Record, vol. 3, pp. 1558-1561.*
Richter et al., Detection of Malignant and Benign Breast Lesions with an Automated US System: Results in 120 Cases, 1997, Radiology, vol. 205, pp. 823-830.*

* cited by examiner

*Primary Examiner* — Toan Ton
*Assistant Examiner* — John Corbett
(74) *Attorney, Agent, or Firm* — Loginov & Sicard; Keri E. Sicard; William A. Loginov (57) ABSTRACT

Disclosed are methods, and associated systems comprising processors, input devices and output devices, of detecting regions of interest in a tomographic breast image. The methods may comprise: acquiring tomographic breast image data; deriving a plurality of synthetic sub-volumes from the tomographic breast image data; wherein each subvolume is defined by parallel planar top and bottom surfaces; wherein planar top and bottom surfaces of successive subvolumes are parallel to each other; and wherein a top planar surface of a sub-volume is offset from a top planar surface of a prior sub-volume, such that successive sub-volumes overlap; for each sub-volume, deriving a two-dimensional image; for each two-dimensional image, identifying regions of interest therein; deriving at least one region of interest of potential clinical interest from a plurality of identified regions of interest; and outputting information associated with at least one derived region of interest of potential clinical interest.

46 Claims, 4 Drawing Sheets

COMPUTER-AIDED DETECTION OF REGIONS OF INTEREST IN TOMOGRAPHIC BREAST IMAGERY

CROSS-REFERENCE TO RELATED APPLICATIONS

This application is a continuation of and claims the benefit of U.S. Provisional Application 61/105,895 filed on Oct. 16, 2008, incorporated herein by reference.

BACKGROUND

In the fields of medical imaging and radiology, various techniques may be employed for creating images of an anatomical region of the human body. For example, in mammography, the breast is often imaged at two fixed angles using x-rays. Physicians may review two-dimensional (2-D) or planar x-ray images of the breast (i.e., mammograms) to uncover and diagnose disease-like conditions, such as breast cancer.

Numerous medical imaging procedures now employ systems and techniques that create three-dimensional (3-D) or volumetric imagery of the human body. For example, significant attention has been given to tomographic imaging techniques. One such example is digital breast tomosynthesis (DBT), a relatively new imaging procedure in which systems image a breast by moving a source and exposing the breast to radiation from a plurality of angles, thus acquiring high resolution, planar images (i.e., "direct projections") at different angles. For example, a DBT system may acquire 10 direct projection images in which the source moves in such a way as to change the imaging angle by a total angle of 40 degrees. From these direct projections, computer software can be used to construct a 3-D volume of the breast (i.e., a "reconstructed volume"). A reconstructed volume may be used to derive a series of 40-60 individual images called slices that are oriented parallel to a single plane of the imaged object (i.e., the "reconstruction plane"). The computer software may reconstruct each slice at a different depth and may use different thicknesses, allowing physicians to visualize the breast and information of interest at various depths of field that were previously unavailable with traditional 2-D imaging systems and procedures.

In mammography, a physician typically may review four images to diagnose a patient: a cranial-caudal (CC) image and a medial-lateral oblique (MLO) image of each of the right and left breasts. In contrast, in tomographic imaging such as DBT, a physician may review any of the direct projections and/or reconstructed volume slices to diagnose a patient. For example, the physician may use an input device in combination with a computer system and graphical user interface (GUI) to "scroll" through slice images displayed on the GUI, so as to simulate moving through the breast perpendicular to the reconstruction plane. Any of these images or combination of images may depict information of interest in a way that allows a physician to detect and diagnose a potential disease-like condition. Thus, while tomographic imaging may allow a physician to improve the overall quality of care to a patient over traditional mammographic imaging, the substantial amount of image data available may have a negative impact on the physician's workload and interpretation time.

Computer-aided detection (CAD) is one solution to help a physician to overcome problems such as workload and interpretation time. Using sophisticated computer algorithms based on image processing and pattern recognition disciplines, CAD systems may detect and present information (e.g., lesions) in medical imagery that may be of interest to a reviewing physician. CAD has enjoyed widespread success in its application to mammographic medical imaging, as it has been shown to improve patient care, reduce human workload, and reduce human error associated with fatigue or variability between observers. More recently, CAD has been proposed and developed to assist physicians moving to tomographic imaging procedures.

Given the increase in the amount of image data acquired by tomographic imaging techniques, several different approaches are feasible in which a computer system can perform CAD and present information of interest to a physician.

CAD may be performed on direct projection images acquired by the system. For example, each individual direct projection may be analyzed. However, direct projections may be noisy and, like mammography, may have a very limited depth of field. Thus, if CAD is performed on the direct projections, important regions may be obscured by other uninteresting tissue in the direct projections and therefore, not detected by CAD.

Alternatively, CAD may be performed on the voxels of the entire reconstructed volume. However, the spatial distortion and noise characteristics of the reconstructed volumes may be complicated, requiring more sophisticated and/or customized algorithms, computational power, computational storage, and computational time. Thus, if CAD is performed on the entire reconstructed volume, the workflow of a physician may be negatively impacted by the speed of such a system. Physicians may require CAD to assist them in reviewing and diagnosing the imagery of numerous patients each day.

Alternatively, CAD may be performed on the individual slices derived from a reconstructed tomographic volume. An overview of such a technique, as well as an overview of the aforementioned techniques, may be found in U.S. Pat. No. 6,748,044, "Computer assisted analysis of tomographic mammography data," assigned to GE Medical Systems Global Technology Company, LLC. While each individual slice may have information about lesions or other structures of interest at a range of depths throughout the object, a lesion or other structure of interest may be spread across a plurality of slices. This may be particularly true if the slices of the tomographic volume are reconstructed with thicknesses that are less than the expected size of the lesion or other structure of interest. Resolving this information may be problematic for a computer system, leading to false detections, missed detections, and/or poorly-represented detections.

It is therefore an object of this disclosure to present methods and systems to automatically detect and present information about lesions and other structures of interest in tomographic imagery of the breast in a manner that is advantageous for use in a clinical setting, both in terms of computational speed and detection accuracy.

SUMMARY

Disclosed are methods, and associated systems comprising processors, input devices and output devices, of detecting regions of interest in a tomographic breast image. The methods may comprise: by means of an input device, acquiring tomographic breast image data; by means of a processor, deriving a plurality of synthetic sub-volumes from the tomographic breast image data; wherein each subvolume is defined by parallel planar top and bottom surfaces; wherein planar top and bottom surfaces of successive subvolumes are parallel to each other; and wherein a top planar surface of a sub-volume is offset from a top planar surface of a prior sub-volume, such that successive sub-volumes overlap; by means of a processor, for each sub-volume, deriving a two-dimensional image; by means of a processor, for each two-dimensional image, identifying regions of interest therein; by means of a processor, deriving at least one region of interest of potential clinical interest from a plurality of identified regions of interest; and by means of an output device, outputting information associated with at least one derived region of interest of potential clinical interest.

In the methods, the tomographic breast image data may be acquired by means of an image acquisition unit. The tomographic breast image data may comprise a tomographic breast volume. The tomographic breast volume may be acquired by means of an image acquisition unit obtaining a plurality of two-dimensional breast images of an anatomical breast at differing angles, and a processor computing the tomographic breast volume from the plurality of two-dimensional breast images. The tomographic breast image data may be acquired from at least one of a computer network and a storage device. The tomographic breast volume may be acquired by obtaining a plurality of two-dimensional breast images of an anatomical breast at differing angles by means of at least one of a computer network and a storage device, computing the tomographic breast volume from the plurality of two-dimensional breast images by means of a processor.

Deriving at least one region of interest of potential clinical interest from a plurality of identified regions of interest may comprise: each region of interest identified in a plurality of two-dimensional images, determining a location of the region of interest; for each located region of interest, deriving a further sub-volume enclosing said located region of interest; and for each located region of interest, further evaluating said located region of interest to determine if it is of potential clinical interest.

Each subvolume may have a same thickness as all other subvolumes. The same thickness may be a predetermined thickness. Each subvolume may be offset from the prior sub-volume by a same offset amount. The same offset amount may be a predetermined offset amount.

Outputting information associated with at least one derived region of interest of potential clinical interest may comprise displaying said at least one derived region of interest in conjunction with at least a portion of a breast image. Information associated with at least one derived region of interest of potential clinical interest may comprise at least one CAD mark. Information associated with at least one derived region of interest of potential clinical interest may comprise a location of the said at least one region of interest.

Each synthetic sub-volume may be derived from a plurality of consecutive thin slices of the tomographic breast volume. Each thin slice may be in the range of about 1 mm. to about 3 mm. thick. A thickness of each subvolume may be in the range of about 3 mm. to about 30 mm. An offset between top planar surfaces of successive sub-volumes may be in the range of about 1 mm. to about 3 mm. An offset between top planar surfaces of successive sub-volumes may be equal to a thickness of a thin slice of a tomographic breast volume.

Each two-dimensional image may be derived by performing an intensity projection algorithm on a subvolume. Each region of interest may be identified by executing a suspicious lesion detection algorithm on a two-dimensional image. The suspicious lesion detection algorithm may identify regions of interest comprising microcalcifications, density masses, and/or spiculated masses.

DETAILED DESCRIPTION

In the following detailed description of embodiments, reference is made to the accompanying drawings that form a part hereof, and in which are shown, by way of illustration and not by way of limitation, specific embodiments in which the methods and systems disclosed herein may be practiced. It is to be understood that other embodiments may be utilized and that logical, mechanical, and electrical changes may be made without departing from the scope of the methods and systems disclosed herein.

Figure 1:
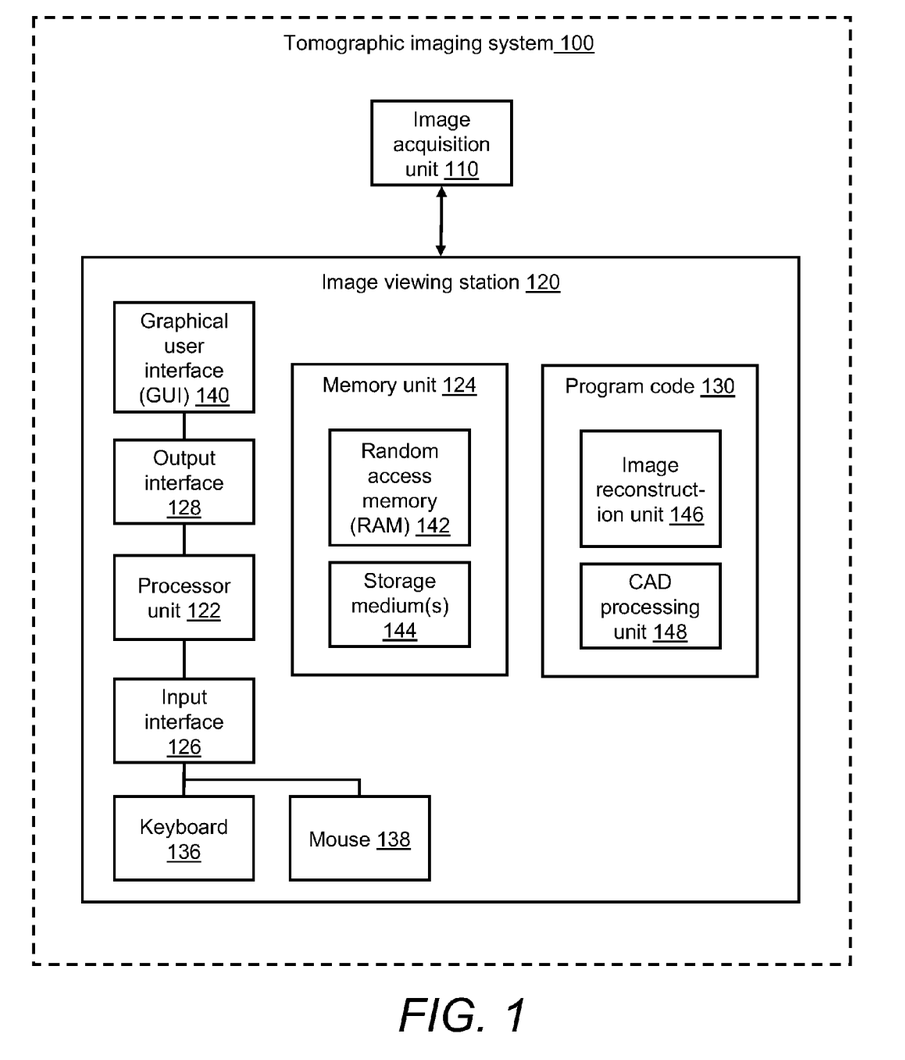
FIG. 1 is a block diagram of an illustrative tomographic imaging system that may be used to perform the methods disclosed herein.

FIG. 1 is a view of an illustrative tomographic imaging system 100 that may be used to perform the methods disclosed herein. Preferably, tomographic imaging system 100 is used in clinical practice to acquire tomographic medical imagery of the breast, automatically detect regions of interest (ROIs) in the imagery, and present the results to a physician. The system described is for reference purposes only; other types and variations of tomographic imaging systems may be employed to acquire tomographic medical imagery for processing in accordance with the methods disclosed herein.

Tomographic imaging system 100 includes an image acquisition unit 110 for performing a tomographic imaging procedure on a patient and an image viewing station 120 for processing and displaying the imagery to a user (e.g., a physician). Image acquisition unit 110 may connect to and communicate with image viewing station 120 via any type of communication interface which may include, but is not limited to, physical interfaces, network interfaces, software interfaces, and the like. Alternatively, it will be understood by a person of skill in the art that image acquisition unit 110 and image viewing station 120 may be deployed in different configurations. For example, and not by way of limitation, image acquisition unit 110 and image viewing station 120 may be parts of a single computer, computer processor or computer system. As another example, image viewing station 120 may be deployed independently of an image acquisition unit, and may retrieve tomographic images from storage devices or over a network or by other communication means as will be known to a person of skill in the art. As still another example, the functions of image viewing station 120 may be divided between two or more processors, so that for example, and not by way of limitation, one processor may perform certain processing according to the methods disclosed herein, while another processor accessible to a user is responsible for other processing steps, and/or communicates with display and input means.

Image acquisition unit 110 is representative of systems that can acquire a series of images of a patient's breast using tomographic imaging procedures. For example, and not by way of limitation, image acquisition unit 110 may be a digital breast tomosynthesis (DBT) imaging system such as offered by the General Electric Company of Fairfield, Conn. (GE); Hologic, Inc, of Bedford, Mass. (Hologic); or Siemens AG of Munich, Germany (Siemens). DBT imaging systems image a breast by moving a source, acquiring a number of projection images (e.g., 10-25 direct projections) at different angles (e.g., at 4 degree increments).

Image viewing station 120 is representative of any system that can perform the automated identification methods disclosed herein, henceforth interchangeably referred to as CAD, on medical imagery acquired by image acquisition unit 110. (As set forth above, in alternative embodiments a plurality of processors may be used, and these processors may be disposed in more than one location, in lieu of using a single integrated image viewing station.) Image viewing station 120 may further output both the medical imagery and results of CAD. Image viewing station 120 may further comprise one or more processor units 122, memory units 124, input interfaces 126, output interfaces 128, and program code 130 containing instructions that can be read and executed by image viewing station 120. One or more input interfaces 126 may connect processor units 122 to input devices such as keyboards 136, mouse devices 138, and/or other suitable devices. Thus, one or more input interfaces 126 allows a user to communicate commands to the processor(s), one such exemplary command being the initiation of automated, computer-aided detection (CAD) methods disclosed herein. Output interface(s) 128 may further be connected to processor unit(s) 122 and one or more output devices such as a graphical user interface (GUI) 140. Thus, an output interface 128 allows image viewing station 120 to transmit data from one or more processor units 122 to an output device, one such exemplary transmission including medical imagery and ROIs identified by CAD for display to a user on the GUI.

Memory unit(s) 124 may be comprised of conventional semiconductor random access memory (RAM) 142 or other forms of memory known in the art; and one or more computer readable-storage mediums 144, such as a hard drive, floppy drive, read/write CD-ROM, tape drive, etc. Stored in program code 130 may be an image reconstruction unit 146 for constructing additional imagery from the images acquired directly by image acquisition unit 110; and a CAD processing unit 148 for automatically identifying ROIs in medical imagery in accordance with the methods disclosed herein.

It is further noted that while image reconstruction unit 146 and CAD processing unit 148 are depicted as being components within image viewing station 120, as discussed above it will be understood by a person of skill in the art that such components may be deployed as parts of separate computers, computer processors, or computer systems. For example, image reconstruction unit 146 may be deployed as part of a tomographic review workstation system (e.g., DexTop Breast Imaging Workstation, Dexela Limited, London, United Kingdom).

General operation of tomographic imaging system 100 for performing the methods disclosed herein is as follows. As one potential prelude to the novel methods disclosed herein, a patient enters image acquisition unit 110 and a series of projection x ray images (i.e., direct projections) of one or both breasts are acquired. Each direct projection may have, for example, a spatial resolution of 85 microns, and dimensions of 3500 rows of pixels by 2800 columns of pixels. Image acquisition unit 110 transfers the direct projections to image reconstruction unit 146, which constructs an image volume of the breast (i.e., a reconstructed tomographic breast volume). Image reconstruction unit 146 optionally may construct a series of individual thin slices using the direct projection image data acquired by image acquisition unit 110. The tomographic breast volume optionally may be constructed in 40-60 image thin slices, each thin slice having a spatial resolution of 100 microns per pixel, a thickness of 1 millimeter (mm), and dimensions of 2500 rows of pixels by 1500 columns of pixels. Of course, other numbers of image thin slices, other spatial resolutions, other thicknesses, and other dimensions,—are possible within the scope of the disclosed methods. Optionally, individual thin slices need not be constructed in association with the reconstructed breast volume.

As is known in the art, the tomographic breast volume may be created by "reconstruction algorithms," which may be implemented as software program modules in a processing unit such as image reconstruction unit 146. A specific example of one reconstruction algorithm can be seen in Claus BEH et al: "A new method for 3D Reconstruction in Digital Tomosynthesis," Medical Imaging 2002, Proceedings of the SPIE, vol. 4684, no. Part 1-3, Feb. 24-28, 2002, pp. 814-824. Other examples of reconstruction algorithms include "shift and add" algorithms and iterative maximum-likelihood expectation maximization (ML-EM) algorithms. It is to be appreciated that the methods disclosed herein are not limited to any one type of reconstruction algorithm used to reconstruct the tomographic breast volume. Either automatically or upon the execution of a command by a user of tomographic imaging system 100, image reconstruction unit 146 may transmit the reconstructed tomographic breast volume to CAD processing unit 148, which may automatically process the imagery to detect regions of interest. This process will be more fully described in reference to FIGS. 2-4. The imagery and CAD processing results may then be outputted via an output device such as GUI 140 to a user for review, such as a physician who may require a computerized assessment of the imagery. Such an assessment may be made in addition to the physician's manual assessment of the imagery using image viewing station 120.

Figure 2:
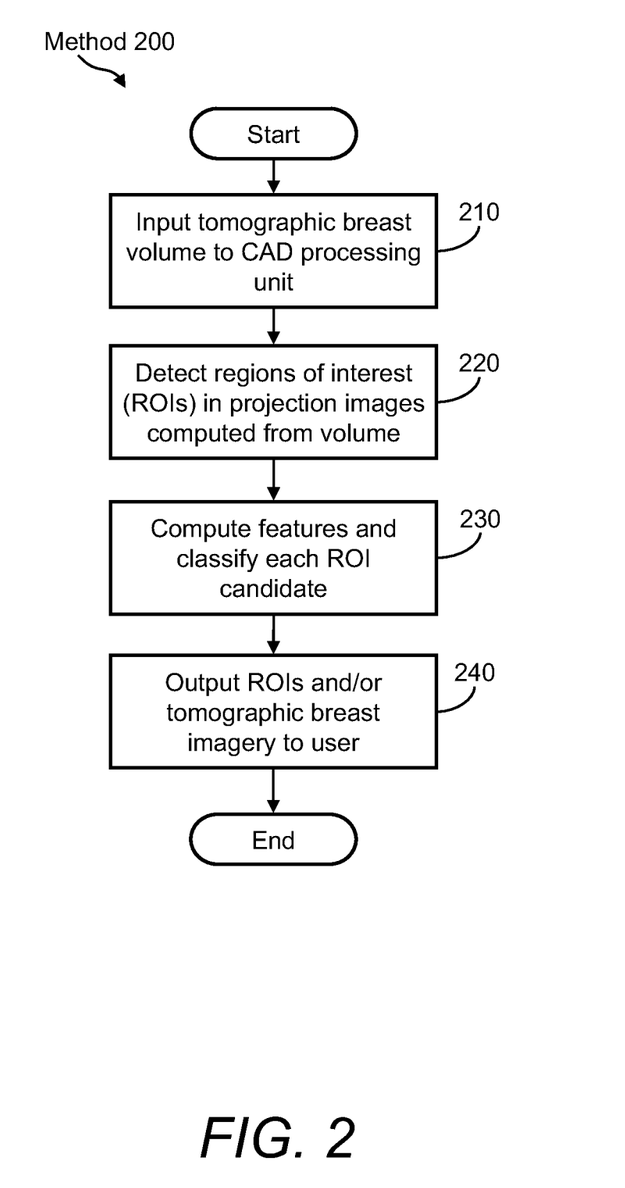
FIG. 2 is a flowchart that illustrates steps that may be performed by a computer system to automatically identify and present suspicious regions of interest (ROIs) in tomographic medical imagery of the breast in accordance with certain embodiments disclosed herein.

FIG. 2 illustrates the steps of a method 200 to automatically identify and present suspicious regions of interest (ROIs) in tomographic medical imagery in accordance with certain embodiments disclosed herein. Such a method may be performed by CAD processing unit 148 in accordance with the general operation of tomographic imaging system 100, for example. Method 200 may overcome the limitations of prior approaches to detecting suspicious ROIs in tomographic image data by computing a plurality of projection images from a reconstructed breast tomographic volume in ways that may enhance the signature or "signal-to-noise" of suspicious ROIs. In certain embodiments to be described, each ROI candidate detected may be further automatically evaluated on an individual basis by the computer system to eliminate false positive detections.

Suspicious ROIs may include any plurality of pixels or voxels that exhibit characteristics that may be of interest to a physician or other user. Exemplary ROIs in the breast include lesions such as micro-calcification clusters or masses, all of which may be indicators of disease states such as breast cancer. False positives such as vascular calcifications, lymph nodes, skin folds, or parenchyma, all of which ultimately may be ruled out as possible indicators of disease states, may also be present. Image reference points such as the nipple, which may be used by a reviewer during interpretation of the data, may also be present. Other abnormalities that may be of interest to a physician or other user of tomographic imaging system 100, or that may be confused with abnormalities of interest, may also be present.

At step 210, a reconstructed volume of tomographic breast data, such as that constructed in accordance with the general operation of tomographic imaging system 100 described above, is input to a processing unit suitable for executing the methods disclosed herein, one such example being CAD processing unit 148.

At step 220, CAD processing unit 148 computes a plurality of computed (i.e., synthetic) projection images from the tomographic breast volume and performs a detection process on each computed projection image. As will be fully described in reference to FIG. 3, each computed projection image is created from a synthetic sub-volume. If thin image slices are available, the synthetic sub-volumes may be created, each using a plurality of the thin image slices available in the tomographic breast volume at different depths of field. Thus, each computed projection image may depict details of the breast at a particular location with greater "thickness" or in-depth (i.e. "out-of-plane") information than that which can be depicted in a single thin slice of the tomographic breast volume or a single direct projection image. In addition, multiple synthetic sub-volumes may be created such that sub-volumes overlap each other. Accordingly, the likelihood that the system will detect each ROI in the imagery is improved because the characteristics of the ROI will be presented with sufficient detail both "in-plane" and "in-depth" in a single sub-volume, rather than being divided between multiple thin slices or even multiple non-overlapping thicker subvolumes.

The detection process involves searching each computed projection image for clusters of pixels or voxels that have the general characteristics of a suspicious ROI. For example, the detection process may search for clusters that are bright, dense, and of a certain size. In further embodiments to be fully described in reference to FIG. 3, a sliding window in effect may be used by the system to move through the entire volume, create the computed projections from sequences of overlapping sub-volumes, and detect candidate ROIs in each sub-volume.

By performing such a process on a set of projection images rather than the entire tomographic breast volume, it should be understood that the computational time in which to detect ROIs may be significantly reduced. This has the advantage of presenting results to a physician or other user of the system with faster speeds than approaches that perform detection on entire reconstructed volumes.

As is known in the art, from a detection process, numerous ROIs may be identified that have suspicious characteristics but are actually non-suspicious (i.e., false positives). The results of detection at step 220 may be used as input to an evaluation process at step 230, where each individual ROI candidate is further evaluated to eliminate false positives. For example, various feature or characteristic measurements (e.g., contrast, brightness, shape, size, density, texture, and/or converging lines) may be computed on a ROI, each of which may or may not indicate suspiciousness. The specific features computed at step 230 will depend on the detection process executed at step 220 and the type of ROI to detect. The values of these features may then be compared against various parameters and rules by a classification process or "classifier," the results of which may be used to determine which an ROI should be presented to a physician or whether an ROI should be disregarded. Examples of such classification algorithms include a linear classifier, a quadratic classifier, a neural network, a decision-tree, a fuzzy logic classifier, a support vector machine (SVM), a Bayesian classifier, or a k-nearest neighbor classifier, and other classification approaches as will be known by a person skilled in the art. The parameters and rules of the classification process may be established by presenting the classifier with sample feature values of true positives and false positives, as is known in the art.

The evaluation process at step 230 may be performed directly using the pixels of each ROI detected in the individual computed projection images. However, it should be recognized that while the projection imagery may computed at step 220 in ways that are satisfactory for detecting the general characteristics of suspicious ROIs, such imagery may not be satisfactory for evaluating the specific characteristics of a suspicious ROI to determine if the candidate warrants outputting to the physician.

Thus, in accordance with certain embodiments, the results of the candidate detection process performed at step 220 may be used to compute additional imagery that is optimized to extract features of single candidate ROIs. For example, a new projection image may be computed at the location of each candidate ROI detected. In such embodiments, each computed image more finely encapsulates a candidate and thus, further maximizes the signature or "signal-to-noise" ratio of a candidate's features. In turn, by computing feature measurements on such imagery, the evaluation results for each candidate will be more accurate. It is also noted that the sample feature values of true positives and false positives in which to establish the parameters and rules of the classification process described at step 230 may also be computed from this improved imagery. This is in contrast to computing the feature values on true positives and false positives in the individual computed projection images, which are better suited for identifying the general characteristics of candidate ROIs.

At step 240, ROIs detected and evaluated as suspicious are output and displayed to a physician or other user of tomographic imaging system 100. For example, suspicious ROIs are typically output and displayed along with imagery of the breast on an output device such as GUI 140, such that a reference is presented as to the location of each suspicious ROI in the patient's breast. For example, the series of individual thin slices of a reconstructed tomographic breast volume may be displayed to a user so as to appear in a "stacked" manner. Each slice may further contain a visual mark corresponding to the pixels or voxels of a suspicious ROI which was identified using the methods disclosed herein.

In clinical practice, tomographic image data may be analyzed in accordance with the methods disclosed herein, but no suspicious ROIs may be identified. This may suggest to a physician that the patient's breast may be normal, healthy, or without indicators of cancer. Thus, in certain embodiments, zero suspicious ROIs may be outputted to a physician. In this case, the absence of suspicious ROIs is as substantially important as the presence of suspicious ROIs. In certain other embodiments, one or more suspicious ROIs may be outputted. This suggests to a physician that the patient's breast may be abnormal, unhealthy, or with cancer indicators. In this case, the physician's attention is drawn to each individual ROI for further evaluation as potential indicators of disease state.

Figure 3:
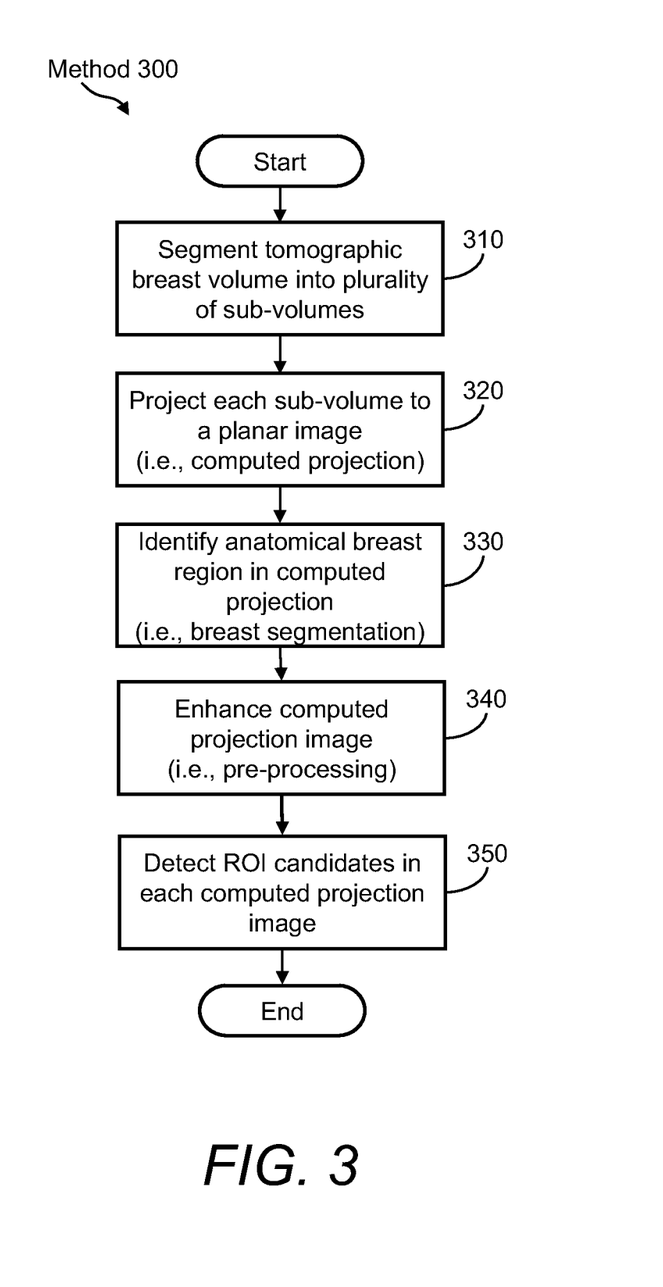
FIG. 3 is a flowchart that illustrates steps that may be performed by a computer system to automatically detect candidate ROIs in tomographic medical imagery of the breast in accordance with certain embodiments disclosed herein.

FIG. 3 illustrates the exemplary steps of a method 300 to automatically detect candidate ROIs in tomographic medical imagery of the breast, such exemplary steps corresponding to one embodiment of step 220 of FIG. 2.

At step 310, the tomographic breast volume is segmented into a plurality of synthetic sub-volumes. Each subvolume may be constructed so as to have planar top and bottom surfaces parallel to each other. The planar surfaces of successive sub-volumes may in turn be parallel with each other. In other embodiments the surfaces of the synthetic sub-volumes need not be planar or parallel. In some embodiments, the surfaces of successive sub-volumes may be parallel to a fixed reconstruction plane. Each subvolume may have a thickness (which may be perpendicular to the reconstruction plane in embodiments with reconstruction planes) such that all ROIs within an expected target abnormality size range will be encapsulated in a single sub-volume. As previously discussed, tomographic breast volumes are typically divided into thin slices such that the "thickness" of each slice in the volume is less than the expected size of a ROI. For example, slice images may be reconstructed with thicknesses of 1-3 mm, while lesions such as masses or micro-calcification clusters may have an expected size ranging anywhere from 3-30 mm. Thus, a single ROI (e.g., ROI 410 illustrated in FIG. 4) may appear in multiple thin slices (e.g., slices 420) of a tomographic breast volume (e.g., tomographic breast volume 400). While a human viewer may prefer such an arrangement while reviewing multiple thin slice images in sequence, for a computer system resolving such artifacts may be troublesome, prone to error, and therefore, suboptimal for an automated detection process. Worse still, a computer system may fail to detect an ROI at all if the overall signature of the ROI is weakly distributed across multiple thin slices. Clusters of micro-calcifications may be particularly problematic, since they may appear as only individual points on each slice.

Figure 4:
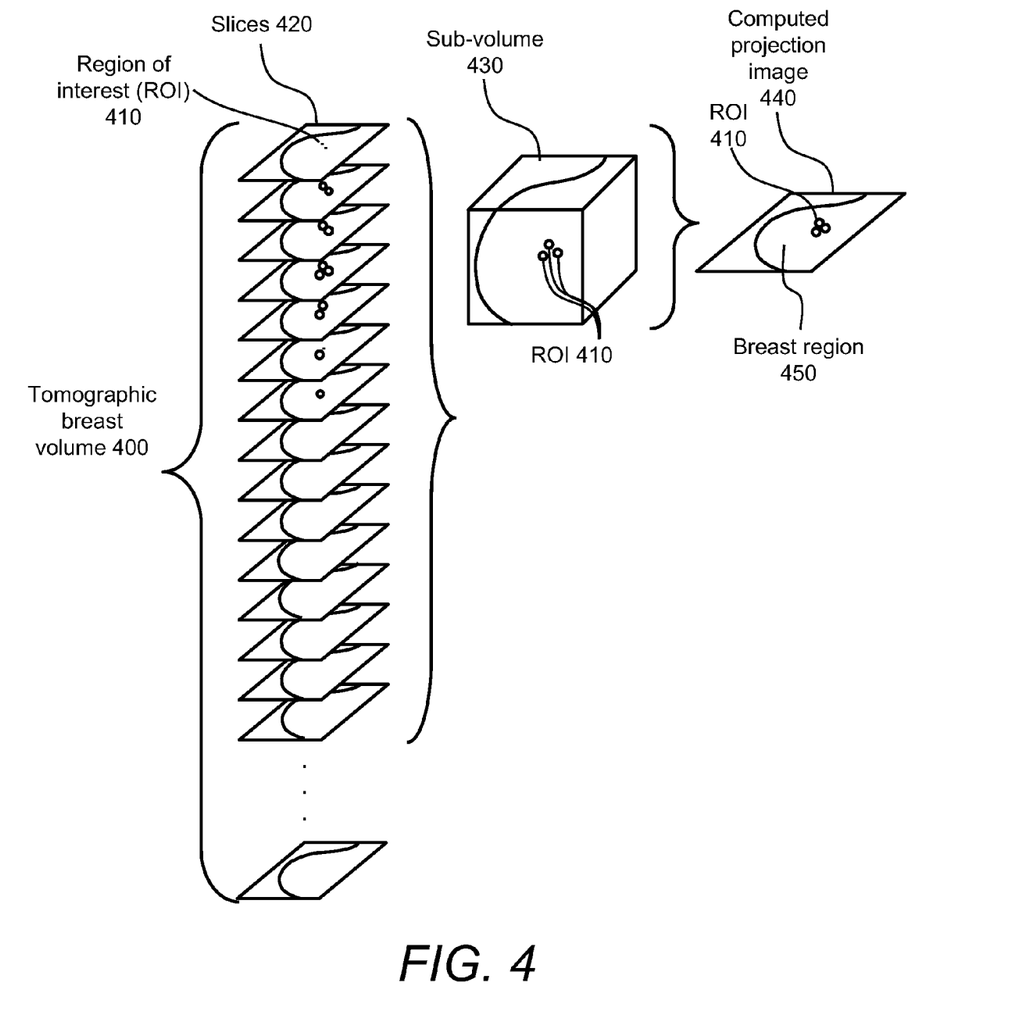
FIG. 4 is an illustration visually depicting how a candidate ROI may appear in projection imagery computed from a tomographic breast volume.

To overcome such issues, each sub-volume according to the methods disclosed herein may be constructed by selecting two or more adjacent thin slice images from the reconstructed volume to form a "thicker" synthetic sub-volume. The specific number of slices used to form a synthetic sub-volume may be determined according to a ratio of maximum target abnormality size to reconstructed volume thin slice thickness. For example, as shown in FIG. 4, presented with a tomographic breast volume 400 of thin slices 420 each having thicknesses of 2 mm, to capture ROIs with a maximum target abnormality size of 30 mm, a synthetic sub-volume of 15 slices (illustrated as sub-volume 430) may be formed. Alternatively, if presented with a tomographic breast volume having thin slices of various thicknesses, a computation such as the average slice thickness across a set of thin slices may be used to set a slice thickness parameter for use in such a ratio.

In some embodiments, the maximum target abnormality size(s) may be stored in image viewing station 120 as one or more predefined parameters. For example, to detect a single mass cancer with the methods disclosed herein, a target abnormality size parameter may be preset within a range of 3-30 mm to detect such lesions. Alternatively, in some other embodiments, the maximum target abnormality size parameter may be defined in CAD processing unit 148 at "run-time" (i.e., during execution of the methods disclosed herein). For example, prior to the execution of step 310, the parameter may be determined by computing an initial, rough estimate as to the maximum dimensions of the ROI appearing in the tomographic breast volume. Exemplary steps in which to compute such an estimate may include projecting the entire tomographic breast volume into a single projection image, executing a detection algorithm on the single projection image, computing an estimate as to the size of each ROI detected, and setting the parameter according to the maximum computed size of an ROI detected. The establishing of such a parameter at "run-time" may further reduce the noise in each projection image around candidate ROIs, leading more accurate detection results.

CAD processing unit 148 need not form sub-volumes from all pixels of a given thin slice or all voxels across thin slices. Sub-volumes may be formed from segments of each thin slice (i.e., specific columns and rows of pixels in each thin slice, or voxels created from multiple thin slices) so as to create sub-volumes of varying dimensions that might best encapsulate a given ROI. Examples include, but are not limited to, cubes, curved slabs, thick slabs, thin slabs, or any other manifold formed from the pixels or voxels of two or more adjacent thin slice images of a tomographic breast volume. For example, if the target ROI to detect is parenchyma, curved slab sub-volumes may be particularly useful, as parenchyma will typically be long, curved strand-like objects.

At step 320, CAD processing unit 148 projects each synthetic sub-volume to a planar, 2-D image (i.e., a computed or synthetic projection image). An example of a computed projection image 440 constructed from sub-volume 430 is illustrated in FIG. 4. Numerous projection algorithms exist that map the voxels of a volume to a 2-D image plane. Any number of these algorithms may be used to perform step 320. One example is a maximum intensity projection (MIP) algorithm. Other projection algorithms may compute the mean or median intensity to form computed projections. The projection may be performed along any axis. In certain embodiments, the projection may be performed perpendicular to and onto the reconstruction plane.

At step 330, the anatomical breast may be identified within each computed projection image (e.g., breast region 450, as shown in FIG. 4) and any pixels outside of this breast region may be excluded from further processing. A number of algorithms are known that identify the breast region area from a cranial-caudal (CC) or medial-lateral oblique (MLO) mammogram. Any of these algorithms may be suitable for performing step 330, particularly if the computed projection images are formed at a similar plane to that used to create conventional mammographic imagery. For example, the algorithm disclosed in U.S. Pat. No. 6,091,841 "Method and system for segmenting desired regions in digital mammograms" by Qualia Computing, Inc., may be performed at step 330. In other embodiments, the breast may be identified using available imagery other than the computed projection images. For example, the entire tomographic breast volume may be projected into a single projection image and the breast region then identified in this image.

In an optional pre-processing step, as illustrated by step 340, CAD processing unit 148 may improve each computed projection image and thus, the efficacy of the methods disclosed herein by performing one or more pre-processing operations known in the art. For example, cropping may be performed to reduce the amount of data to be processed in subsequent steps, or filtering may be performed to enhance the ROIs to be detected. Other pre-processing operations might further include, but are not limited to, smoothing, noise reduction, sharpening, etc.

At step 350, ROI candidates are identified in each computed or synthetic projection image. As is known in the art, numerous mass detection algorithms exist that identify lesions based on measurements of the core or density in the imagery, numerous spiculation detection algorithms exist that identify lesions based on measurements of spiculated lines extending from mass-like regions in the imagery, and numerous micro-calcification detection algorithms exist that identify lesions based on measurements related to the cluster of individual calcification points around a neighboring area. Examples of such detection algorithms can be seen in U.S. Pat. Nos. 5,999,639, "Method and system for automated detection of clustered microcalcifications from Digital Mammograms"; 6,137,898, "Gabor filtering for improved microcalcification detection in digital mammograms"; 6,167,146, "Method and system for segmentation and detection of microcalcifications from digital mammograms"; 6,205,236, "Method and system for automated detection of clustered microcalcifications from digital mammograms"; 6,389,157, "Joint optimization of parameters for the detection of clustered microcalcifications in digital mammograms," all of which are assigned to Qualia Computing, Inc. and are incorporated herein by reference; and U.S. Pat. Nos. 6,801,645, "Computer aided detection of masses and clustered microcalcifications with single and multiple input image context classification strategies;" and 7,298,877, "Information fusion with Bayes networks in computer-aided detection systems," all of which are assigned to iCAD, Inc. and are incorporated herein by reference. Any of the detection algorithms disclosed in these references or other prior art references may be performed in accordance with the type of ROI to detect.

In accordance with further embodiments, sub-volumes and associated computed projection images may be constructed from thin slice images in an overlapping manner. More specifically, each sub-volume and associated computed projection image may be constructed from: at least one thin slice image of the tomographic breast volume, a subset of the pixels of at least one thin slice image of the tomographic breast volume, or a subset of the voxels of a plurality of thin slice images of the tomographic breast volume that are also used to construct at least one other computed projection image. In certain embodiments, the overlap may be set equal to the thickness of individual thin slices in the volume so that potential candidates in a given slice are captured in at least two sub-volumes and associated computed projection images.

CAD processing unit 148 may perform the detection methods disclosed herein on the image volume in an overlapping manner using a sliding window technique or mode. For example, given a 10 cm thick reconstructed tomosynthesis volume with an individual thin slice thickness of 2 mm and a maximum expected target size parameter of 25 mm, a CAD system may move through the volume using a sliding window of 2 mm increments at a sub-volume thickness of 25 mm. CAD processing unit 148 will obtain a first 25 mm thick sub-volume of imagery from 1-26 mm in depth in the volume, compute a first projection image from this sub-volume, and identify candidate ROI detections within the first computed projection. CAD processing unit 148 will then slide to the next 25 mm thick sub-volume of imagery from 3-28 mm in depth in the volume, compute a second projection image from this sub-volume, identify candidate ROI detections within the second computed projection, etc. An advantage of using a sliding window technique is the computational speed improvements gained in which the various processing components of tomographic imaging system 100 (e.g., processor unit 122, memory unit 124, etc.) are provided access to the tomographic imagery (e.g., blocks of pixels or voxels) to perform the methods disclosed herein.

Without the use of overlap as disclosed herein, CAD processing unit 148 may detect a single ROI separately across multiple sub-volumes and associated computed projection images. Such a situation may occur even if the sub-volume thickness is set to be larger than the maximum size of an ROI appearing in the volume, as it will not be known at which image slices the ROI will appear, begin, or end. Using an overlapping technique as disclosed herein, a given ROI may appear in multiple computed projection images, but the "signal-to-noise" ratio or signal of that ROI will be strongest in a single computed projection. The overlapping technique thus allows a computation as to the image thin slice in which a given ROI begins and the image thin slice in which a given ROI ends, which may be particularly useful information for a candidate evaluation process such as the evaluation process introduced at step 230 and more fully described below.

It should be recognized that the candidate detection process described in reference to FIG. 3 is a "coarse" approach in which many potential ROIs (i.e., candidates) are identified. This "coarse" approach detects candidates with high sensitivity and at acceptable processing speeds. While feature measurements may be computed on candidates detected in imagery created using such approach, doing so may lead to unacceptable sensitivity and false positive rates. For example, candidate ROIs may be detected that have a size substantially less than the maximum target abnormality size parameters used to create each computed projection image and thus, a significant amount of noise may exist in the surrounding area of the ROI. Such noise may not be sufficiently minimized to the point where specific features or characteristics of each candidate may be measured with sufficient accuracy. For example, it may be suboptimal to compute features on a 5 mm candidate ROI in a projection image created by projecting 30 mm of slice imagery.

To overcome these problems, the results of the candidate detection process performed at step 220 may be used as input to the candidate evaluation process performed at step 230. For example, features of each candidate ROI detected at step 220, such as the location in which the candidate appears in the computed projection, may be used to determine the location of the candidate in the tomographic breast volume. CAD processing unit 148 may perform any number of forward projection algorithms that are known in the art to make such a determination.

In accordance with certain embodiments, volumetric features (i.e., "3-D" features) may be computed directly on a volumetric representation of each candidate ROI. Exemplary volumetric features that may be computed include curvature, aspect ratio, volume, crossing line, contrast features, etc. Volumetric features may be computed to measure characteristics of suspiciousness (e.g. malignancy, non-malignancy) that cannot be accurately measured in planar projection images.

Alternatively, in accordance with certain embodiments, from the location of an ROI in the tomographic breast volume, a new projection image may be computed that more finely encapsulates the individual ROI. For example, referring back to FIG. 4, a computed projection may be formed using seven thin slice images, determined based on the location of an ROI detected in a projection image computed from 15 thin slices. Planar features may then be computed on the planar or 2-D representation of the ROI. Exemplary planar features include contrast, brightness, shape, size, density, texture, converging lines, etc.

It is further noted that a combination of volumetric features and planar features may be computed on any given ROI and input to a classification process such as that described in reference to step 230. More specifically, a single vector of both volumetric and planar features may be formed. The use of this combination vector by a classification process to measure suspiciousness may lead to more reliable classification results than if only volumetric features or if only planar features are measured and used to classify a ROI.

Any of the projection images computed at either the candidate detection or candidate evaluation processes may be output to the physician at step 240 as a means for the physician to visualize a detected ROI. The projection images computed at the candidate evaluation process may be particularly useful for the physician, as each of these computed projections may present a planar representation of the ROI with sufficient detail both "in-plane" and "in-depth" for the physician to review the ROI.

For example, now referring back to step 240, the series of individual thin slices of a reconstructed tomographic breast volume may be displayed to a user on GUI 140 so as to appear in a "stacked" manner. Each slice may further contain a visual mark corresponding to the pixels or voxels of a suspicious ROI which was identified using the methods disclosed herein. Upon command from the physician who uses keyboard 136 and/or mouse 138 to select or "query" a suspicious ROI for more detail, the projection image computed to perform the evaluation process at step 230 may be retrieved from memory unit 124 and displayed on GUI 140. This projection image may be displayed so as to appear superimposed over the individual slice image also depicting the ROI.

The methods disclosed herein automatically detect regions of interest in tomographic imagery of the breast in a manner that is acceptable for use in a clinical setting, both in terms of computational speed and accuracy. The speed of such a method is optimized by first performing a "coarse" detection process on a plurality of computed projection images, each of which may contain a candidate region of interest (ROI). The accuracy of the detection process described herein may be optimized by creating the computed projection images from a plurality of thin slices at a specific "thickness" that may be predefined in the system or, alternatively, computed at run-time. The use of a sliding window to perform the detection process in an overlapping manner may further improve the accuracy of the method. Each candidate ROI may then be individually evaluated using a more computationally intensive or "fine" evaluation process, which includes the computation of feature characteristics and classification using the feature characteristics.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the disclosures herein or the methods and systems defined in the appended claims. More specifically, although some aspects of the present disclosure may be identified herein as preferred or particularly advantageous, it is contemplated that the present disclosure is not limited to these preferred aspects.

The invention claimed is:

1. A method of detecting regions of interest in a tomographic breast image using a system, the system comprising a processor, an input device, and an output device, the method comprising the steps of:
    a) acquiring tomographic breast image data by means of the input device;
    b) deriving a plurality of synthetic sub-volumes from the tomographic breast image data by means of the processor;
        wherein each sub-volume is defined by parallel planar top and bottom surfaces;
        wherein planar top and bottom surfaces of successive sub-volumes are parallel to each other; and
        wherein a top planar surface of a sub-volume is offset from a top planar surface of a prior sub-volume, such that successive sub-volumes overlap;
    c) deriving a two-dimensional image by means of a processor for each sub-volume;
    d) identifying regions of interest therein for each two-dimensional image, by means of the processor that identifies a plurality of identified regions of interest by searching for general characteristics of a suspicious region of interest;
    e) computing values associated with at least one identified region of interest of the plurality of identified regions of interest to indicate a level of suspiciousness of the at least one region of interest, by means of the processor; and
    f) outputting information associated with at least one derived region of interest of potential clinical interest by means of the output device.

2. The method of claim 1, wherein the tomographic breast image data is acquired by means of an image acquisition unit.

3. The method of claim 1, wherein the tomographic breast image data comprises a tomographic breast volume.

4. The method of claim 3, wherein the tomographic breast volume is acquired by means of an image acquisition unit obtaining a plurality of two-dimensional breast images of an anatomical breast at differing angles, and a processor computing the tomographic breast volume from the plurality of two-dimensional breast images.

5. The method of claim 1, wherein deriving at least one region of interest of potential clinical interest from a plurality of identified regions of interest comprises:
    e1) for each region of interest identified in a plurality of two-dimensional images, determining a location of the region of interest;
    e2) for each located region of interest, deriving a further sub-volume enclosing said located region of interest; and
    e3) for each located region of interest, further evaluating said located region of interest to determine if it is of potential clinical interest.

6. The method of claim 1, wherein each sub-volume has a same thickness as all other sub-volumes.

7. The method of claim 6, wherein the same thickness is a predetermined thickness.

8. The method of claim 1, wherein each sub-volume is offset from the prior sub-volume by a same offset amount.

9. The method of claim 8, wherein the same offset amount is a predetermined offset amount.

10. The method of claim 1, wherein outputting information associated with at least one derived region of interest of potential clinical interest comprises displaying said at least one derived region of interest in conjunction with at least a portion of a breast image.

11. The method of claim 10, wherein information associated with at least one derived region of interest of potential clinical interest comprises at least one Computer aided detection (CAD) mark.

12. The method of claim 10, wherein information associated with at least one derived region of interest of potential clinical interest comprises a location of the said at least one region of interest.

13. The method of claim 1, wherein each synthetic sub-volume is derived from a plurality of consecutive thin slices of the tomographic breast volume.

14. The method of claim 13, wherein each thin slice is in the range of about 1 mm. to about 3 mm. thick.

15. The method of claim 1, wherein a thickness of each sub-volume is in the range of about 3 mm. to about 30 mm.

16. The method of claim 15, wherein an offset between top planar surfaces of successive sub-volumes is in the range of about 1 mm. to about 3 mm.

17. The method of claim 15, wherein an offset between top planar surfaces of successive sub-volumes is equal to a thickness of a thin slice of a tomographic breast volume.

18. The method of claim 1, wherein each two-dimensional image is derived by performing an intensity projection algorithm on a sub-volume.

19. The method of claim 1, wherein each region of interest is identified by executing a suspicious lesion detection algorithm on a two-dimensional image.

20. The method of claim 19, wherein the suspicious lesion detection algorithm identifies regions of interest comprising microcalcifications, density masses, and/or spiculated masses.

21. The method of claim 1, wherein the wherein the value comprises feature or characteristic measurements including: contrast, brightness, shape, size, density, texture or converging lines.

22. The method of claim 1, further comprising the step of comparing at least one of the values associated with the at least one region of interest to a classifier to determine a level of suspiciousness of the at least one region of interest.

23. The method of claim 22 wherein the classifier comprises a linear classifier, a quadratic classifier, a neural network, a decision-tree, a fuzzy logic classifier, a support vector machine (SVM) a Bayesian classifier or a k-nearest neighbor classifier.

24. A system for detecting regions of interest in a tomographic breast image, comprising: at least one input device, configured to acquire tomographic breast image data;
at least one processor, configured to:
   a) derive a plurality of synthetic sub-volumes from the tomographic breast image data;
   wherein each sub-volume is defined by parallel planar top and bottom surfaces;
   wherein planar top and bottom surfaces of successive sub-volumes are parallel to each other; and
   wherein a top planar surface of a sub-volume is offset from a top planar surface of a prior sub-volume, such that successive sub-volumes overlap;
   b) for each sub-volume, derive a two-dimensional image;
   c) for each two-dimensional image, identify regions of interest therein that identify a plurality of identified regions of interest by searching for general characteristics of a suspicious region of interest;
   d) compute values associated with at least one identified region of interest of the plurality of identified regions of interest to indicate a level of suspiciousness of the at least one region of interest; and
   at least one output device, configured to output information associated with at least one derived region of interest of potential clinical interest.

25. The system of claim 24, wherein the tomographic breast image data is acquired by means of an image acquisition unit.

26. The system of claim 24, wherein the tomographic breast image data comprises a tomographic breast volume.

27. The system of claim 26, wherein the tomographic breast volume is acquired by means of an image acquisition unit obtaining a plurality of two-dimensional breast images of an anatomical breast at differing angles, and a processor computing the tomographic breast volume from the plurality of two-dimensional breast images.

28. The system of claim 24, wherein the tomographic breast image data is acquired from at least one of a computer network and a storage device.

29. The system of claim 28, wherein the tomographic breast image data comprises a tomographic breast volume.

30. The system of claim 29, wherein the tomographic breast volume is acquired by obtaining a plurality of two-dimensional breast images of an anatomical breast at differing angles by means of at least one of a computer network and a storage device, computing the tomographic breast volume from the plurality of two-dimensional breast images by means of a processor.

31. The system of claim 24, wherein deriving at least one region of interest of potential clinical interest from a plurality of identified regions of interest comprises:
   d1) for each region of interest identified in a plurality of two-dimensional images, determining a location of the region of interest;
   d2) for each located region of interest, deriving a further sub-volume enclosing said located region of interest; and
   d3) for each located region of interest, further evaluating said located region of interest to determine if it is of potential clinical interest.

32. The system of claim 24, wherein each sub-volume has a same thickness as all other sub-volumes.

33. The system of claim 32, wherein the same thickness is a predetermined thickness.

34. The system of claim 24, wherein each sub-volume is offset from the prior sub-volume by a same offset amount.

35. The system of claim 34, wherein the same offset amount is a predetermined offset amount.

36. The system of claim 24, wherein outputting information associated with at least one derived region of interest of potential clinical interest comprises displaying said at least one derived region of interest in conjunction with at least a portion of a breast image.

37. The system of claim 36, wherein information associated with at least one derived region of interest of potential clinical interest comprises at least one CAD mark.

38. The system of claim 36, wherein information associated with at least one derived region of interest of potential clinical interest comprises a location of the said at least one region of interest.

39. The system of claim 24, wherein each synthetic sub-volume is derived from a plurality of consecutive thin slices of the tomographic breast volume.

40. The system of claim 39, wherein each thin slice is in the range of about 1 mm. to about 3 mm. thick.

41. The system of claim 24, wherein a thickness of each sub-volume is in the range of about 3 mm. to about 30 mm.

42. The system of claim 41, wherein an offset between top planar surfaces of successive sub-volumes is in the range of about 1 mm. to about 3 mm.

43. The system of claim 41, wherein an offset between top planar surfaces of successive sub-volumes is equal to a thickness of a thin slice of a tomographic breast volume.

44. The system of claim 24, wherein each two-dimensional image is derived by performing an intensity projection algorithm on a sub-volume.

45. The system of claim 24, wherein each region of interest is identified by executing a suspicious lesion detection algorithm on a two-dimensional image.

46. The system of claim 45, wherein the suspicious lesion detection algorithm identifies regions of interest comprising microcalcifications, density masses, and/or peculated masses.

* * * * *